US007807451B2

(12) United States Patent
Kanegasaki

(10) Patent No.: US 7,807,451 B2
(45) Date of Patent: Oct. 5, 2010

(54) APPARATUS FOR DETECTING CELL CHEMOTAXIS

(75) Inventor: Shiro Kanegasaki, Tokyo (JP)

(73) Assignee: ECI, Inc., Tokyo (JP)

( * ) Notice: Subject to any disclaimer, the term of this patent is extended or adjusted under 35 U.S.C. 154(b) by 701 days.

(21) Appl. No.: 10/542,189

(22) PCT Filed: Apr. 8, 2004

(86) PCT No.: PCT/JP2004/005088

§ 371 (c)(1),
(2), (4) Date: Jul. 14, 2005

(87) PCT Pub. No.: WO2004/090090

PCT Pub. Date: Oct. 21, 2004

(65) Prior Publication Data

US 2006/0121600 A1    Jun. 8, 2006

(30) Foreign Application Priority Data

Apr. 9, 2003  (JP) .............................. 2003-105197

(51) Int. Cl.
*G01N 33/48* (2006.01)
*C12M 1/00* (2006.01)
*C12M 3/00* (2006.01)
*C12M 1/42* (2006.01)
*C12M 1/34* (2006.01)

(52) U.S. Cl. .............. 435/288.3; 435/288.5; 435/288.7; 435/285.1; 435/285.2; 435/285.3; 436/63

(58) Field of Classification Search .............. 435/288.3, 435/285.2, 285.3, 288.7, 288.5, 285.1; 436/63
See application file for complete search history.

(56) References Cited

U.S. PATENT DOCUMENTS 3,888,770 A    6/1975  Avital et al.

(Continued)

FOREIGN PATENT DOCUMENTS

DE    19917848 A1    10/2000

(Continued)

OTHER PUBLICATIONS

Kikuchi et al., Microchannel Array Flow Analyzer for measurement of Whole Blood Rheology and Flow Characteristics of Leukocytes Activated by Bacterial Stimulation, Feb. 1997, The International Society of Optical Engineering, vol. 2978, pp. 165-171.*

(Continued)

*Primary Examiner*—Walter D Griffin
*Assistant Examiner*—Lydia Edwards
(74) *Attorney, Agent, or Firm*—Birch, Stewart, Kolasch & Birch, LLP

(57) ABSTRACT

The present invention relates to an improvement in an apparatus for detecting chemotaxis of cells. It aims at providing a structure for detecting chemotaxis of cells at an elevated accuracy with the use of a microquantity of cells. That is to say, an object of the present invention is to provide an apparatus for detecting chemotaxis of cells by which cell injection and position control can be easily carried out while ensuring the prevention of unexpected migration of the cells definitely positioned in a well or the injected sample so that a stable concentration gradient due to the diffusion of the specimen can be maintained and which ensures further automated operation and controlling.

Namely, an apparatus for detecting chemotaxis of cells with a structure wherein two wells are connected to each other via a channel having resistance to the passage of cells and each well has an opening for injecting cells or a specimen, characterized by having (1) a means of transporting a liquid and a means of stopping the transportation after the injection or the aspiration discharge of the liquid and (2) a means of sealing the opening(s) in one or both of the cell-injection side and the specimen-injection side.

24 Claims, 15 Drawing Sheets

U.S. PATENT DOCUMENTS

| | | | |
|---|---|---|---|
| 3,929,583 | A | 12/1975 | Sharpe et al. |
| 4,317,726 | A | 3/1982 | Shepel |
| 4,493,815 | A | 1/1985 | Fernwood et al. |
| 4,514,495 | A | 4/1985 | Schalkowsky et al. |
| 4,714,674 | A | 12/1987 | Palladino |
| 4,729,949 | A | 3/1988 | Weinreb et al. |
| 4,833,382 | A | 5/1989 | Gibbs |
| 4,895,805 | A | 1/1990 | Sato et al. |
| 4,912,057 | A | 3/1990 | Guirguis et al. |
| 5,023,054 | A | 6/1991 | Sato et al. |
| 5,284,753 | A | 2/1994 | Goodwin, Jr. |
| 5,302,515 | A | 4/1994 | Goodwin, Jr. |
| 5,744,366 | A * | 4/1998 | Kricka et al. ............ 436/63 |
| 6,238,874 | B1 | 5/2001 | Jarnagin et al. |
| 6,395,505 | B2 | 5/2002 | Goodwin, Jr. |
| 2002/0009796 | A1 | 1/2002 | Goodwin, Jr. |
| 2002/0086280 | A1 | 7/2002 | Lynes et al. |
| 2003/0003570 | A1 | 1/2003 | Kanegasaki et al. |
| 2003/0003571 | A1 | 1/2003 | Kanegasaki et al. |

FOREIGN PATENT DOCUMENTS

| | | |
|---|---|---|
| EP | 0368241 A2 | 5/1990 |
| JP | 257366/1991 | 11/1991 |
| JP | 23967/1996 | 1/1996 |
| JP | 165062/1999 | 6/1999 |
| JP | 2002-159287 A | 6/2002 |
| WO | WO-94/16098 A1 | 7/1994 |
| WO | WO-96/03206 A1 | 8/1996 |
| WO | WO 98/52691 * | 11/1998 |
| WO | WO-98/52691 A1 | 11/1998 |
| WO | WO-00/07007 A1 | 2/2000 |
| WO | WO-01/32827 A1 | 5/2001 |
| WO | WO 02/30486 A2 | 4/2002 |
| WO | WO-02/46355 A1 | 6/2002 |

OTHER PUBLICATIONS

Boyden, Department of Experimental Pathology, John Curtin School of Medical Research, Australian National University, Canberra, pp. 453-466 (1961).

Francis et al., Proc. Natl. Acad. Sci. USA, vol. 94, pp. 12258-12262 (Nov. 1997).

Kikuchi, Microvascular Research, vol. 50, pp. 288-300 (1995).

Kobayashi et al., J. Biochem, vol. 117, pp. 758-765 (1995).

Lehninger, Biochemistry, Second Edition, The Molecular Basis of Cell Structure and Function, pp. 173-181 (1978).

Mazumder et al., Journal of Crystal Growth, vol. 224, pp. 165-174 (2001).

Cutler, J. et al., Proc. Soc. Exp. Biol. Med., 147: 471-474 (1974).

John, T. J. et al., Life Science, 18:177-182 (1976).

Harvath, L. et al., Journal of Immunological Methods, 37:39-45 (1980).

Zigmond, S. H. et al., Annual Review of Medicine, 37:149-155 (1986).

Falk, W. et al., Journal of Immunological Methods, 33:239-247(1980).

Gatewood, B. et al., Journal of Immunology, 147:243-246(1991).

Falk, W. et al., Infection and Immunity; 36:450-454(1982).

Harvath, L. et al., Infection and Immunity, 36:443-449(1982).

Richards, K. K. et al., Immunological Communications, 13:49-62(1984).

Nelson, R. D. et al., J. Immunol., 115:1650-1656(1975).

Repo, H., Stand. J. Immunol., 6:203-209(1977).

Junger, W. G. et al., J. Immun. Methods, 160:73-79(1993).

Kikuchi, Y. et al., Microvascular Research, 44:226-240(1992).

Kikuchi, Y. et al., SPIE 2978:165-171(1997).

Kikuchi, Y. et al., Journal of the Japan Society for Precision Engineering, 62:1553-1556(1996).

Kikuchi, Y. et al., Chemical Engineering, 62:136-138(1998).

Kikuchy, Y. et al., Biophysics 37:254-258(1997).

Zigmond, S. H., J. Cell Biology 75:606-616(1977).

Allen, W. E. et al., J. Cell Biology, 141:1147-1157(1998).

Zicha, D. et al., J. Cell Science 99:769-775(1991).

Neuro Probe, Inc. "Neuro Probe Zigmond Chamber".

Weber Scientific, Inc. "Dunn Chemotaxis Chamber".

Fisher et al., J. Cell Biology, vol. 108, pp. 973-984 (1989).

Hayamizu et al., Sensors and Actuators A, vol. 103, pp. 83-87 (2003).

Supplementary European Search Report dated Jul. 6, 2009.

* cited by examiner (1)

(2)

(1)

(2)

(1)

(2)

(1)

(2)

(1)

(2)

(3)

(1)

(2)

(3)

(1)

(2)

APPARATUS FOR DETECTING CELL CHEMOTAXIS

TECHNICAL FIELD

This invention relates to an apparatus for detecting chemotaxis of cells. More particularly, it relates to an apparatus by which chemotaxis of cells can be detected by using a microquantity of cells and which has a structure ensuring to easily control cell positioning in a microwell and maintain a stable concentration gradient of a specimen such as a chemotactic factor in a channel.

BACKGROUND ART

As will be discussed hereinafter, the present inventors have made several proposals about apparatuses for detecting chemotaxis of cells by which chemotaxis of cells can be detected with the use of a microquantity of cells by supplying a cell suspension into a well, supplying a specimen into another well and examining whether or not the cells migrate toward the well containing the specimen via a channel provided between the wells. Use of an apparatus for detecting chemotaxis of cells enabling the observation and detection at the single cell level and allowing measurement with the use of about 10 to 100 cells, if possible, offers such advantages that scarce cells can be easily examined and cell reactions can be quantitatively analyzed and studied. In a structure wherein individual wells, which are connected to each other via channels, have each a cell injection port and a specimen injection port, wells together form a connecting tube via the channels and, in its turn, a liquid frequently migrates in the channels. In the step of injecting a specimen such as cells into a well, namely, there frequently arises an increase in pressure, which results in unexpected migration of cells or the specimen in many cases. In the case wherein wells are not completely leveled after the injection or micromovements occur on the liquid level due to, for example, vibration, the transportation of the liquid in the channel is amplified so as to frequently cause migration of cells or a specimen. Such unexpected migration of cells or a specimen causes confusion in the judgment whether the specimen is a chemotactic factor or not. To accurately detect the migration of cells, which perceive the concentration gradient due to the diffusion of the specimen, toward a well containing a specimen, it is therefore required to strictly prevent the unexpected migration of the liquid in the wells involving the channels. To further exactly understand the chemotaxis of cells, it is desirable that individual cells are located in the same state in a well, i.e., forming a line toward a channel, at starting.

The present inventors have previously proposed that, in the case of injecting or aspirating a sample into a well having a tube for injecting/aspirating a sample such as a cell or a chemotactic factor with a micropipette or the like, a rapid change in pressure in a well can be relieved and unexpected migration of the sample in the well can be prevented by providing another tube connecting to the tube for injecting or aspirating the sample (JP-A-2002-159287). In this case, use is made of the structure wherein the pressure in injecting or aspirating a sample is dispersed through the connecting tube.

The present inventors have further proposed a microsample treatment apparatus such as an apparatus for detecting chemotaxis of cells wherein, in a structure comprising a plural number of wells being connected to each other via a part having resistance to fluids and individual wells being provided with tubes for injecting/aspirating a sample and, if necessary, tubes for relieving pressure changes at the injection/aspiration, these tubes have a space in common at the top ends thereof in which a liquid can be held (WO 02/46356). By employing the structure wherein all of the tubes provided in individual wells have a space in common at the top ends thereof in which a liquid can be held, the migration of a liquid at the step of injecting a sample and thereafter can be prevented. In this apparatus, moreover, the positions of the injected cells in a well can be controlled so as to align the cells along the start line at one end of a channel. For this purpose, this apparatus has a means of precisely controlling the injection/discharge of a liquid in a well.

To align cells injected into a well along the start line at one end of a channel, the liquid in the well should be moved and delicate control is required therefor. To prevent the subsequent migration of the liquid in the channel, it is also required to return the liquid into the space at the top ends of the tubes. That is, complicated and strictly controlled procedures are necessary therefor.

In addition to the present inventors' proposals as described above, there has been known an apparatus for detecting chemotaxis of cells wherein wells containing cells and a specimen are connected to each other via channels and the wells are provided with a means of sealing injection ports for the cells and the specimen if necessary (U.S. Pat. No. 5,744,366). In this apparatus, however, cell positioning cannot be controlled in a well and it is therefore impossible to adjust the conditions of the cells at starting.

An object of the present invention is to further improve such an apparatus and thus provide a structure for detecting chemotaxis of cells at an elevated accuracy with the use of a microquantity of cells. Namely, an object of the present invention is to provide an apparatus for detecting chemotaxis of cells by which cells or a specimen can be easily injected and position control of the injected cells can be easily carried out while ensuring the prevention of unexpected migration of the cells definitely positioned in a well or the injected specimen so that a stable concentration gradient due to the diffusion of the specimen can be maintained and which ensures further automated operation and controlling.

RELATED DOCUMENTS

1. JP-A-2002-159287
2. WO 02/46356
3. U.S. Pat. No. 5,744,366

DISCLOSURE OF THE INVENTION

The present invention relates to: (1) an apparatus for detecting chemotaxis of cells with a structure wherein two wells are connected to each other via a channel and each well has an opening for injecting cells or a specimen, which has a means of transporting a liquid for controlling positioning of cells suspended in the well and a means of stopping the transportation after the injection or the aspiration discharge of the liquid, and a means of sealing the opening(s) in one or both of the cell-injection side and the specimen-injection side.

As a preferable example of (2) a member having both of the means of transporting a liquid and the means of stopping the transportation, a pulse pump or a syringe can be cited.

As a preferable example of (3) the means of sealing the opening, a flexible stopper, a slide-type switching member, a tap, a valve or a combination thereof may be cited.

In an embodiment of the present invention, an apparatus for detecting chemotaxis of cells comprising a substrate having two wells provided in both sides of a bank and a glass substrate pressed against the substrate, wherein a channel having resistance to the passage of suspended cells is formed between the bank and the glass substrate, may be cited. In this apparatus, the substrate has an opening for transporting a liquid between the substrate and the glass substrate. The opening has a means/member of transporting a liquid by injection or aspiration and discharge and then stopping the transportation. Further, one of the wells formed in the substrate has a cell-injection port while the other well has a specimen-injection port. Moreover, a means/member of sealing one or both of these injection ports is provided.

In this case, a channel having resistance to the passage of suspended cells is formed between the bank provided on the substrate and the glass substrate. Further, a terrace may be provided in the upper part of the bank to form a gap fit for the diameter or deformability of cells between the terrace and the glass substrate. It is also possible to form a barrier having one or more grooves having a width fit for the diameter or deformability of cells in the terrace on the bank in the channel. If necessary, a gap fit for the diameter or deformability of cells can be formed between the barrier and the glass substrate too. Moreover, arrays of the barriers constituting the grooves may be formed at two positions on the terrace in the channel. It is also possible that multistage terraces are formed on the bank in the channel so as to form gaps with different depths between the terraces and the glass substrate.

In another embodiment, the present invention provides a structure wherein the substrate and the glass substrate are integrated together and at least one of the faces thereof is transparent.

The present invention includes in its scope an integration apparatus for detecting chemotaxis of cells consisting of a plural number of units of the same or different types with the use of the above-described apparatus for detecting chemotaxis of cells as a single unit. Moreover, it includes an integration apparatus for detecting chemotaxis of cells consisting of a plural number of integration units of the same or different types with the use of the above-described integration unit as a single unit.

BRIEF DESCRIPTION OF DRAWINGS

FIGS. 9(1) and (3) are sectional views, while (2) and (4) are respectively top plan views. In this figure, an arrow indicates the transportation direction of the liquid filling up the apparatus.

DESCRIPTION OF REFERENCE NUMERALS

Figure 1:
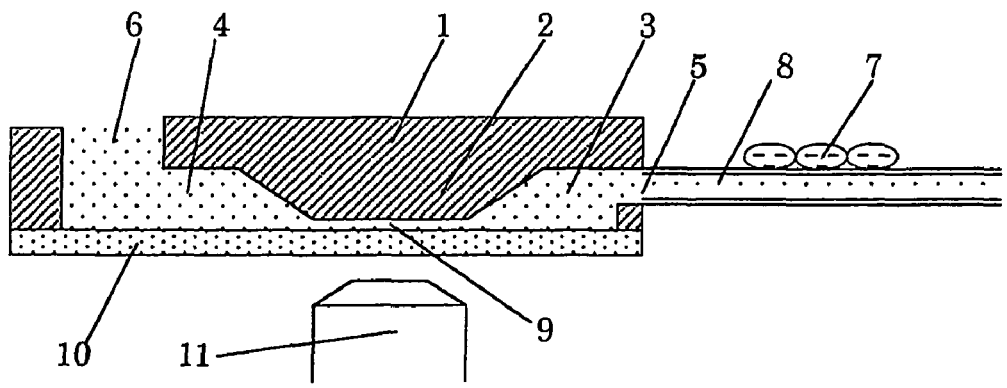
FIG. 1 is a model view showing an example of an apparatus for detecting chemotaxis of cells in which cells are brought together at one end of a bank through the transportation of a liquid from the cell-injection port side. In this figure, an arrow indicates the transportation direction of the liquid filling up the apparatus.
Figure 1:
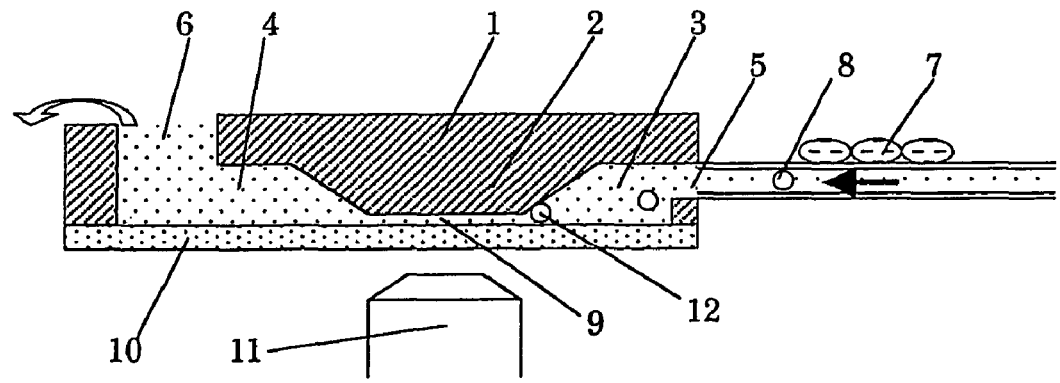

1: substrate
2: bank
3: cell-holding well
4: specimen-holding well
5: cell-injection port
6: specimen-injection port
7: pulse pump
8: injection pipe
9: channel having resistance to the passage of cell
10: glass substrate
11: detector
12: cell
13: syringe
14: liquid-injection means
15: cell suspension tank
16: valve
17: slide-type switching member
18: liquid-injection port
19: flexible stopper
20: cell injector
21: aspiration discharge pipe
22: specimen injector
23: terrace
24: barrier
25: groove in the direction toward the opposite well across channel
26: mark for positioning on screen

BEST MODE FOR CARRYING OUT THE INVENTION

The apparatus for detecting chemotaxis of cells according to the present invention is an apparatus having a structure wherein two wells are connected to each other via a channel having resistance to the passage of cells. After supplying a cell suspension in one of these wells, the cells are aligned at one end of the channel. Next, a specimen is supplied into the other well. Thus the passage of the cells perceiving the concentration gradient of the specimen toward the well holding the specimen can be observed or the cells under passage or having been passed can be counted.

The channel having resistance to the passage of cells as described above means a flow path for cells having a gap through which a cell in the non-adsorbed state (usually having a spherical shape) cannot pass but a cell changing into a flat shape due to its deformability can pass. The term "deformability" of a cell as used herein means that, in case of a flexible cell, the cell can easily change its shape (for example, into flat or string-shaped cells) owing to the flexibility and thus can pass through a gap having a smaller size than the diameter of the cell being in the inherent spherical shape in a free space.

The characteristic of the apparatus for detecting chemotaxis of cells according to the present invention resides in, in addition to the fundamental structure as discussed above, having a means of injecting or aspirating/discharging a liquid for controlling cell positioning in a well and a means of stopping the transportation of the liquid after the aspiration discharge, and, furthermore, having a means of sealing the opening(s) in one or both of the cell-injection side and the specimen-injection side after the injection of cells into the well. By providing the means of transporting cells by injecting or aspirating/discharging a liquid, the cells can be easily aligned along the start line at one end of the channel. By sealing the opening(s) in one or both of the cell-injection side and the specimen-injection side, no movement of the liquid level arises in the wells constituting a connecting tube via the channel and, in its turn, no transportation of the liquid arises in the channel. That is to say, it is possible to prevent cells from unexpected migration in the channel or a change in the concentration gradient of the specimen formed in the channel even though the apparatus is vibrated. The means of stopping the transportation of a liquid is needed in order to completely seal the opening(s) after the injection or the aspiration discharge of the liquid.

Next, this structure will be illustrated by referring the model views FIGS. 1(1) and (2). A raised bank 2 is formed on a substrate 1 and a channel 9 having resistance to the passage of cells is formed between the bank 2 and a glass substrate 10. First, a cell suspension is supplied by a liquid-injection means (a pulse pump 7 in FIG. 1) from a cell-injection port 5 into a cell-holding well 3 via an injection pipe 8. The cells are brought together at one end of the channel 9 having resistance to the passage of cells due to the flow of the liquid and the excessive liquid is discharged from a specimen-injection port 6 (see 12 in (2)). Since a cell transported to the end of the channel 9 blocks the liquid flow, the liquid flow passes through a cell-free part. As a result, the space is filled up with other cells and thus cells are aligned at the end of the channel 9. Although it is not necessary to strictly define the injection speed of the cell suspension, it is favorable to control the transportation speed to about 30 to 40 μm/sec in the case of, for example, using neutrophils or eosinophils and the channel gap size being 5 μm. Next, the liquid transportation is stopped by the pulse pump 7 and the injection pipe 8 is closed, thereby sealing the cell-injection port. Then a chemotactic factor is injected from a specimen-injection port 6. Since the cell-injection port is sealed in this step, the back-flow of the liquid can be prevented and the alignment of the cells at one end of the channel 9 is not disordered. Also, no unexpected migration of the liquid arises in the channel. Thus, the cells perceive the concentration gradient of the specimen (for example, a chemotactic factor) having been stably formed in the channel 9, undergo deformation and thus migrate toward the specimen-holding well side via the channel 9. The passage is observed through the glass substrate 10 by using a detector 11.

As an example of the pulse pump to be used as the liquid-injection means, an apparatus for pulsing liquid transportation in small portions through a liquid-transport pipe, which is driven by compressed air pressure, may be cited. By using this apparatus, a liquid can be quantitatively transported at an order of 1 μl to 1/10 μl. It is also possible to seal the transport pipe. As such an apparatus, for example, there has been known MSL Active Microfluidic Chip Control Hardware (trade name) marketed from Fluidigm Corporation (South San Francisco, Calif.). In addition to the above-mentioned one, there has been known an apparatus with the use of the vibration of a piezoelectric element as a means of pulsing liquid transportation. Use can be made of any of these apparatuses as the liquid-injection means in the present invention. Since a pipe cannot be sealed in the apparatus with the use of the vibration of a piezoelectric element, it is necessary to separately provide a sealing means in the case of using it.

Figure 2:
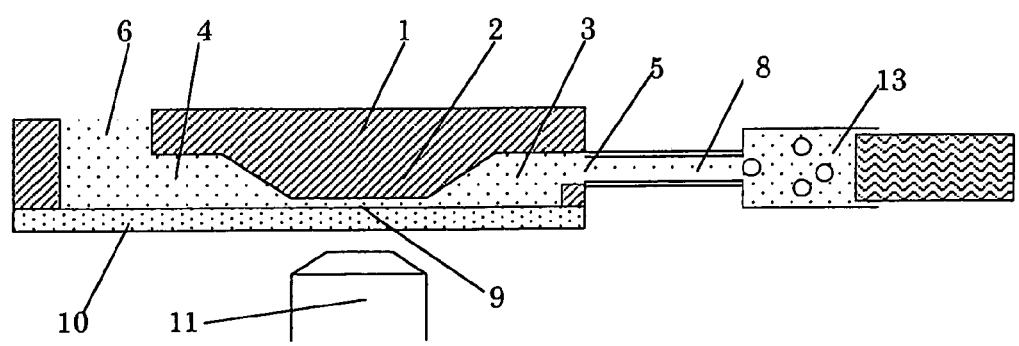
FIG. 2 is a model view showing a case wherein a syringe is employed as a substitute for the pulse pump shown in FIG. 1.

As the liquid-injection means, it is also possible to employ various means other than a pulse pump. For example, use can be made of a syringe represented by 13 in FIG. 2. By using this syringe which is driven by a stepping motor (also called a pulse motor), a liquid can be quantitatively transported. It appears favorable to use this syringe, since the injection port 5 is self-sealed by stopping the liquid transportation without causing back-flow of the liquid.

Figure 3:
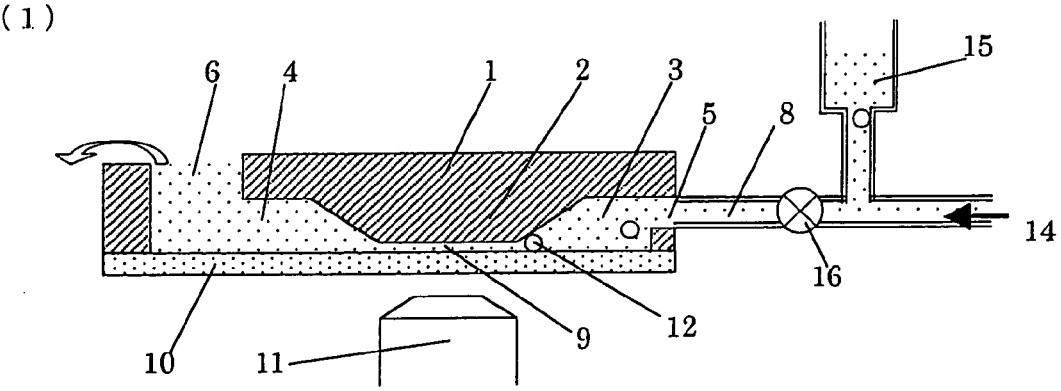
FIG. 3 is a model view showing a case of using a valve as a sealing means. In this figure, an arrow indicates the transportation direction of the liquid filling up the apparatus.
Figure 3:
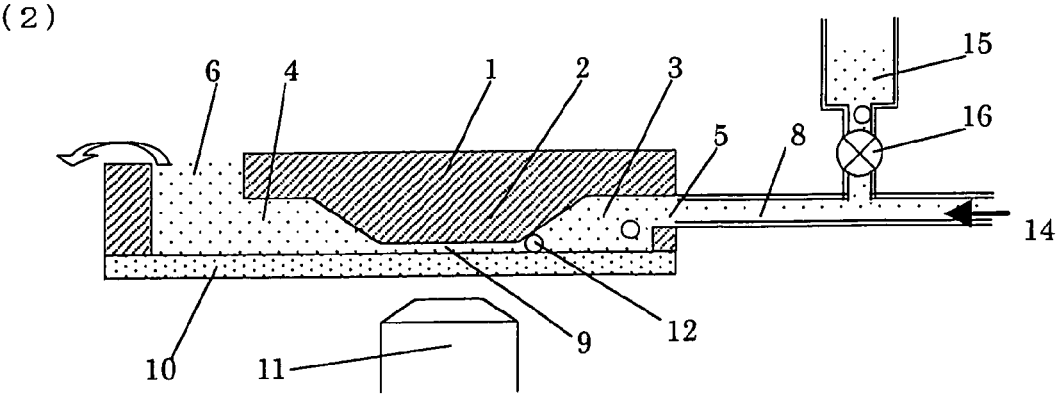

It is also possible to seal the injection port by using a valve as shown in, for example, FIGS. 3(1) and (2). FIG. 3(1) shows a case wherein a valve 16 is provided in an injection pipe 8, while (2) shows a case wherein a valve 16 is provided between a cell suspension tank 15 and an injection pipe 8. In FIG. 3, 14 stands for a liquid-injection means such as a pulse pump or a syringe. The valve 16 may be substituted by another member having a function comparable to a valve. For example, the liquid flow can be stopped by deforming a pipe made of a flexible and elastic material under pressure.

Figure 4:
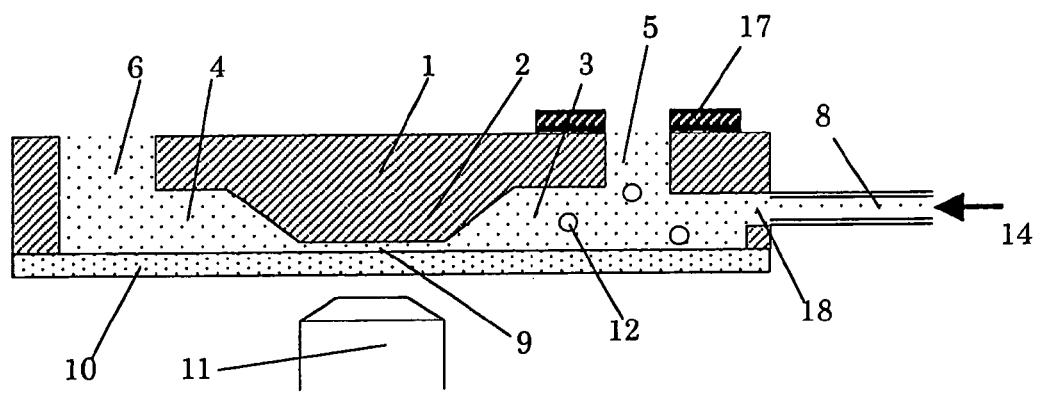
FIG. 4 is a model view showing a case of using a slide-type switching member as a sealing means.
Figure 4:
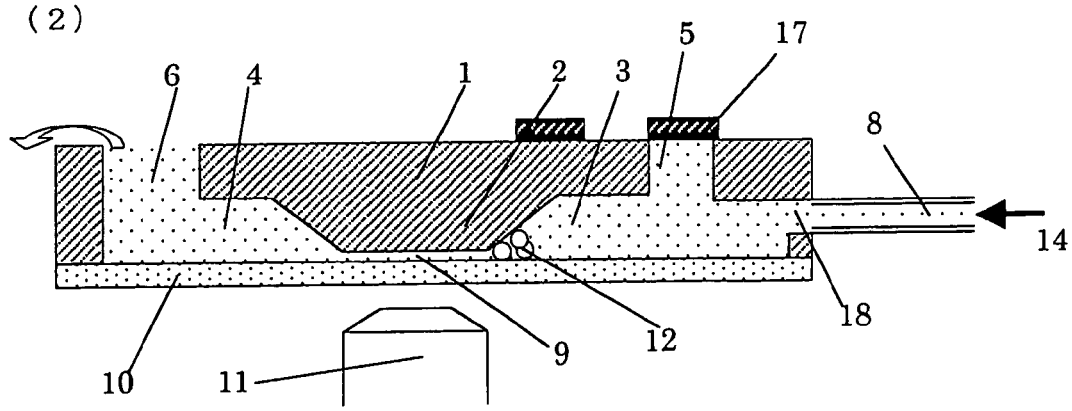

The cell-injection port or the specimen-injection port formed on the substrate can be sealed by various means. For example, use can be made of a slide-type switching member represented by 17 in FIG. 4. FIG. 4(1) shows a case wherein a cell-injection port 5 is open for injecting cells. After injecting the cells from the cell-injection port 5, the cell-injection port 5 is closed by sliding the slide-type switching member 17 as shown in (2). Next, the thus injected cells migrate on the flow of a liquid (for example, a buffer solution), which is supplied by a liquid-injection means 14 and transported through an injection pipe 8, to the end of a channel 9. After the migration of the cells, the pipe 8 is sealed with the use of a means appropriately selected from the above-described ones. The slide-type switching member can be easily switched with the use of, for example, a stepping motor with controllable rotation speed.

Figure 5:
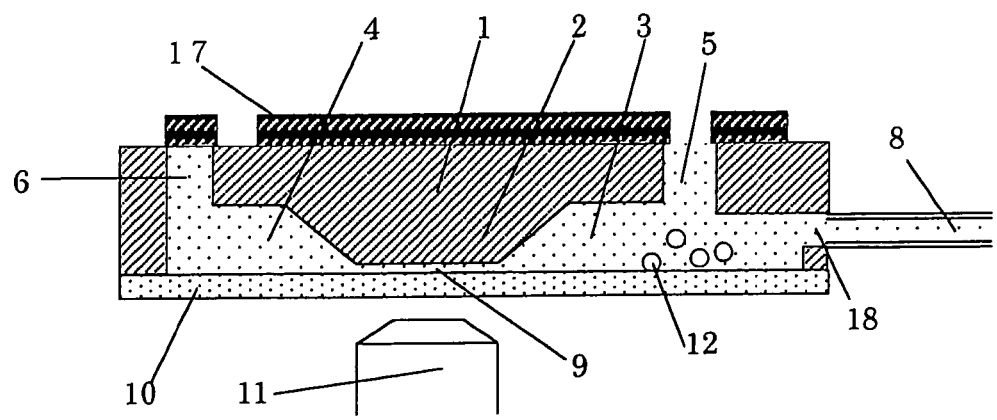
FIG. 5 is a model view showing a case wherein a specimen-injection port is switched on/off in addition to the structure as shown in FIG. 4.
Figure 5:
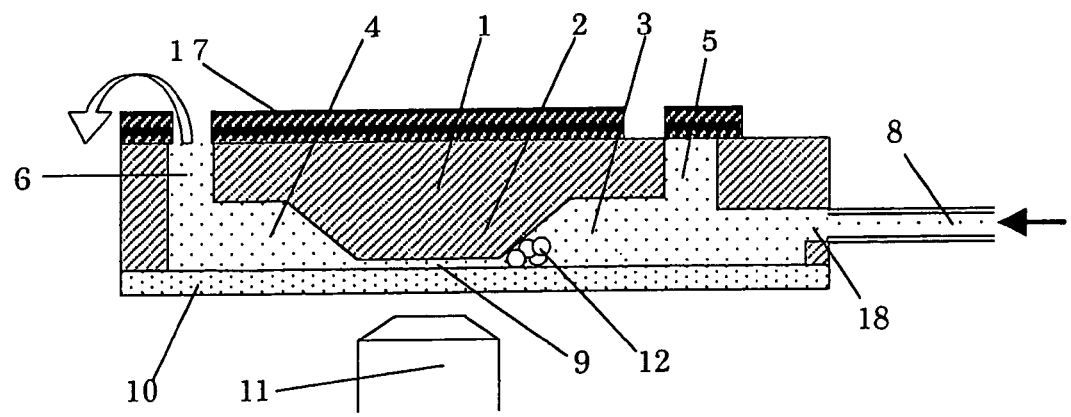

FIG. 5 shows a modification of the structure shown in FIG. 4. FIG. 5(1) shows a case wherein a specimen-injection port 6 is closed when a cell-injection port 5 is opened, while (2) shows another case wherein a specimen-injection port 6 is opened when a cell-injection port 5 is closed.

Figure 6:
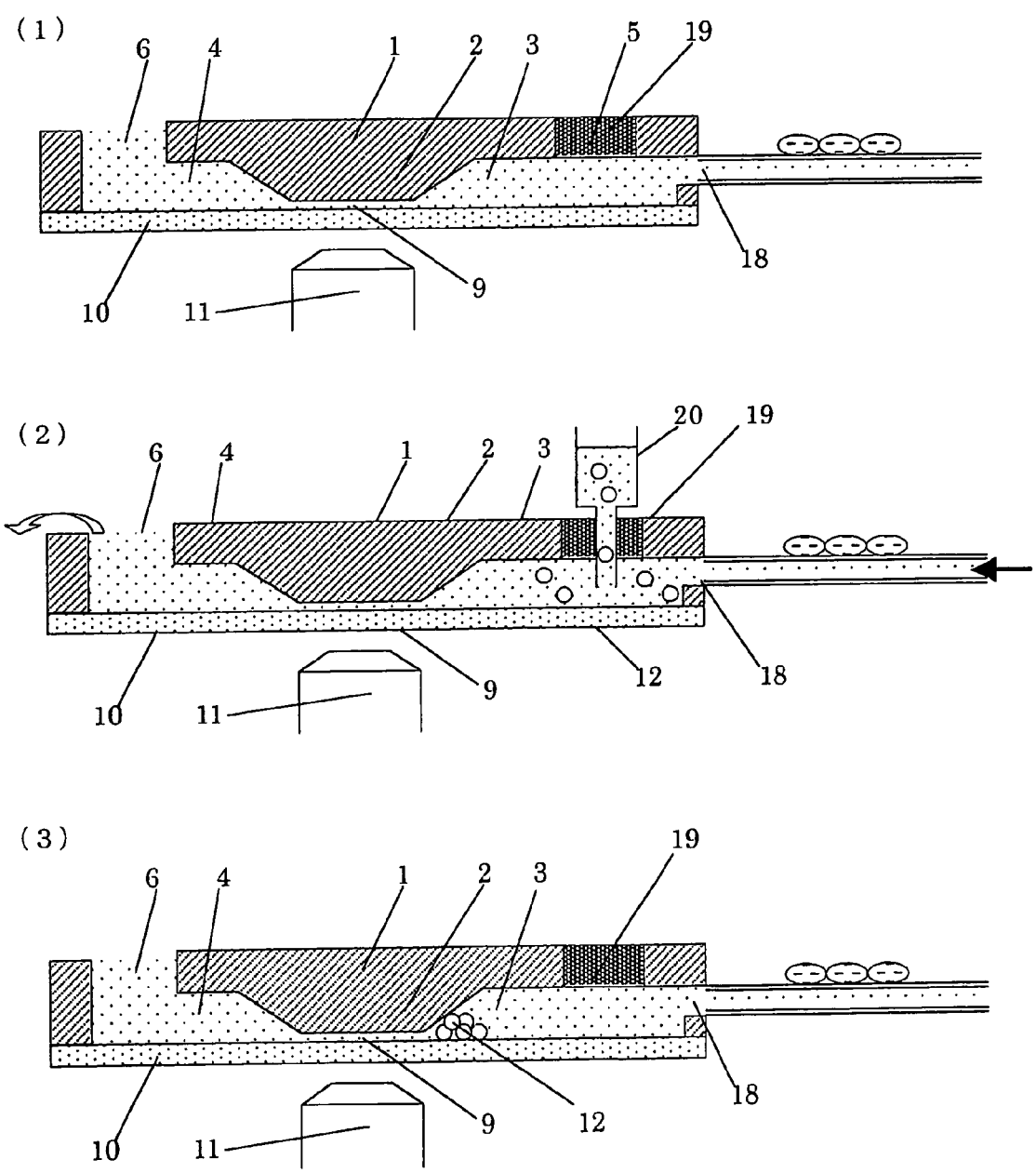
FIG. 6 is a model view showing a case of using a flexible stopper as a sealing means.

FIG. 6 shows a case wherein a cell-injection port 5 is sealed with a flexible stopper 19. Namely, the cell-injection port 5 is tightly sealed with the stopper made of, for example, a filmy silicone rubber, polyurethane, polyethylene, crude rubber or the like having a high elasticity (FIG. 6(1)). Cells are injected by using a cell injector 20 penetrating through the stopper 19 (FIG. 6(2)). After injecting the cells, the injector 20 is drawn out. Thus, the hole in the stopper 19 is filled up owing to its elasticity and the cells 12 are brought together at an end of the channel 9 by the transported liquid flow (FIG. 6(3)). As a substitute for the stopper, it is also possible to employ a tap or the like which is lightly closed in usual but easily allows the penetration of the injector.

Figure 7:
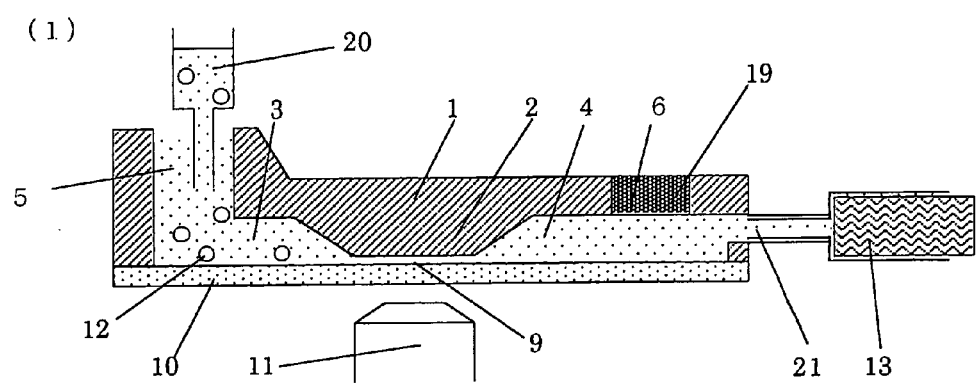
FIG. 7 is a model view showing an example of an apparatus for detecting chemotaxis of cells in which cells are brought together at one end of a bank through the aspiration and discharge of a liquid from the specimen-injection port side. In this figure, an arrow indicates the transportation direction of the liquid filling up the apparatus.
Figure 7:
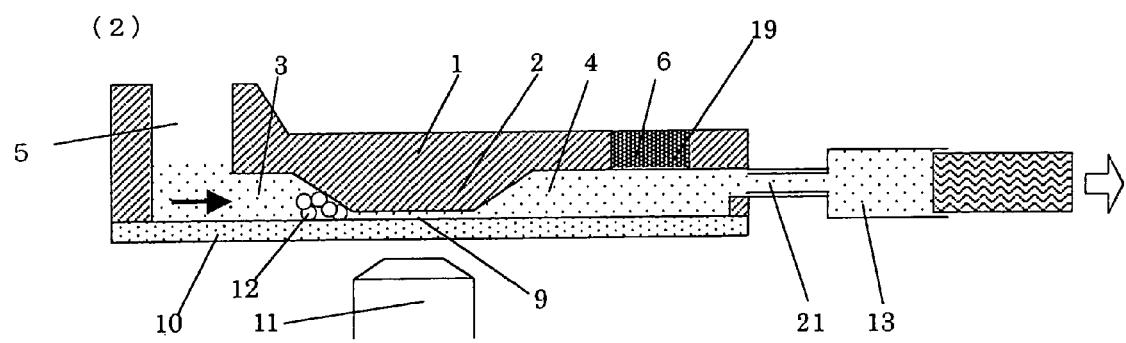
Figure 7:
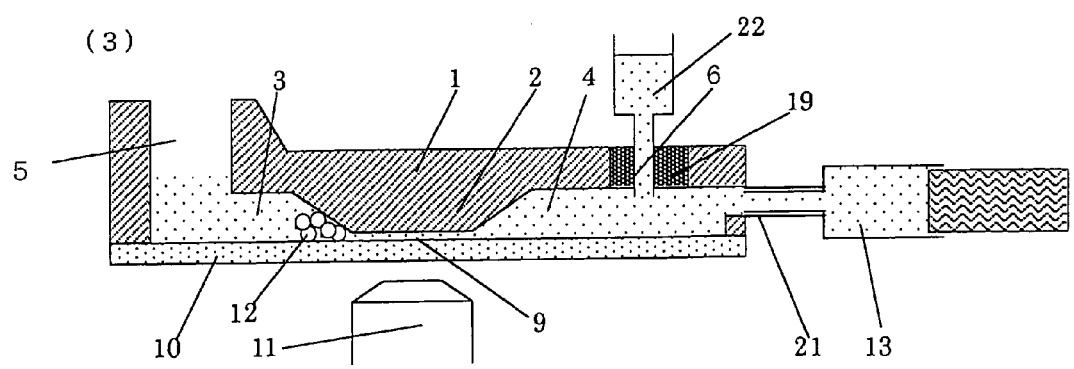

As a substitute for the structures of FIGS. 1 to 6, moreover, use can be also made of a structure shown in, for example, FIG. 7 wherein a liquid is aspirated and discharged from the side of a specimen-holding well 4, which is located in the opposite side to a cell-holding well 3 having a bank 2 between them, and thus cells 12 are brought together at one end of a channel 9 of a cell-holding well 3. Although the liquid is aspirated with a syringe 13 in FIG. 7, it may be substituted by another means having a similar function such as a pulse pump.

Figure 8:
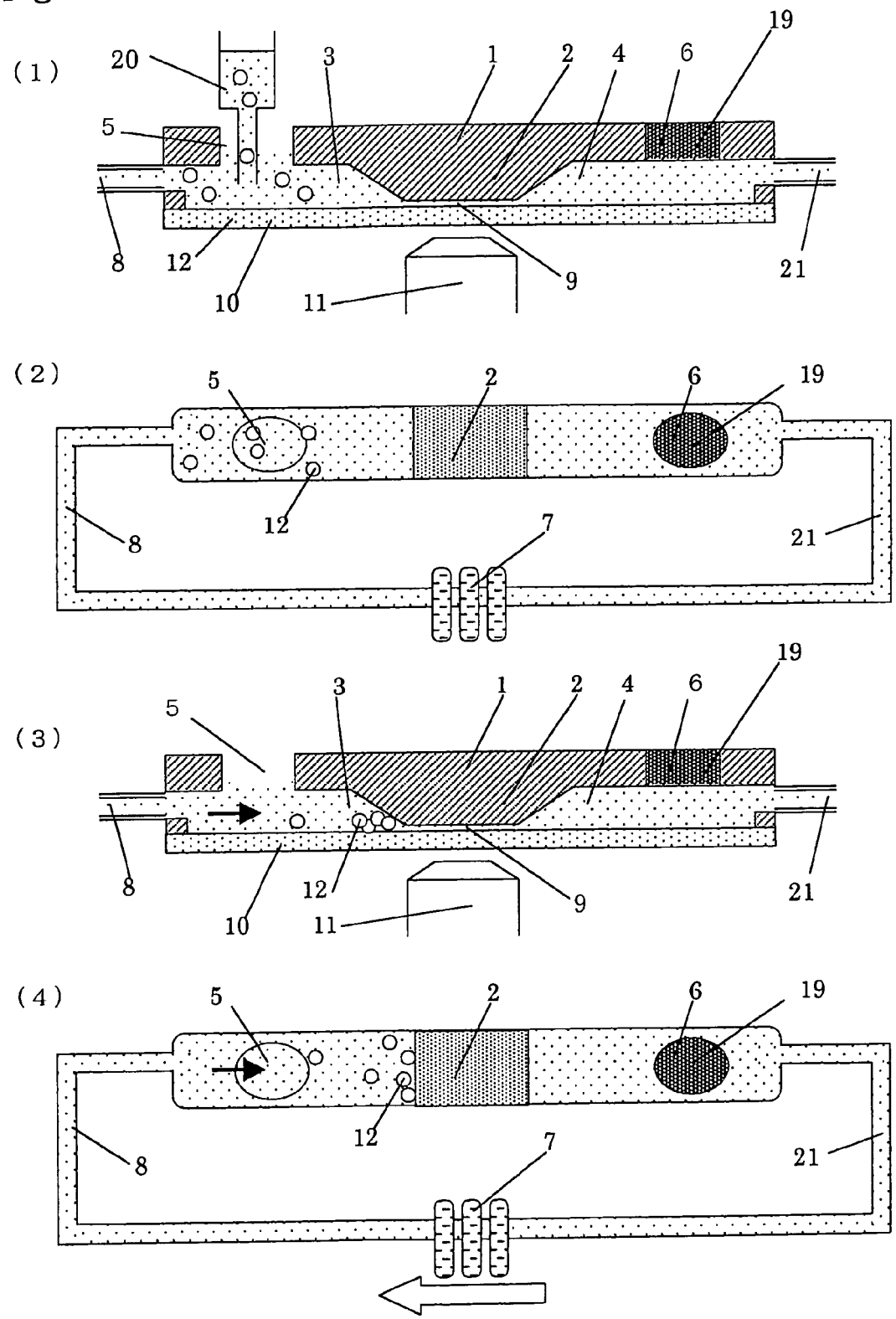
FIG. 8 is a model view showing a structure of the same type as in FIG. 7 wherein a liquid is circulated. In this figure, an arrow indicates the transportation direction of the liquid filling up the apparatus.

The apparatus according to the present invention may have a structure in which a liquid (a medium of the cell suspension) is circulated. FIGS. 8(1) to (4) present model views of such an apparatus. FIG. 8(1) shows a case wherein a cell-holding well 3 has an injection pipe 8 while a sample-holding well 4 has an aspiration discharge pipe 21 and a specimen-injection port is sealed with a flexible stopper 19. As FIG. 8(4) shows, the liquid is circulated by using a means of transporting the liquid in a single direction, for example, a pulse pump 7. FIGS. 8(1) and (2) show each a case wherein cells are injected from the cell-injection port 5, while FIGS. 8(3) and (4) show each a case wherein the liquid is transported in the direction indicated by an arrow so as to bring the cells together at one end of a channel 9. In this case, a chemotactic factor is injected from the specimen-injection port 6 through the stopper 19. The specimen-injection port 6 may be sealed with the use of a means other than the stopper, for example, a slide-type switching member, a valve, a tap or the like.

Figure 9:
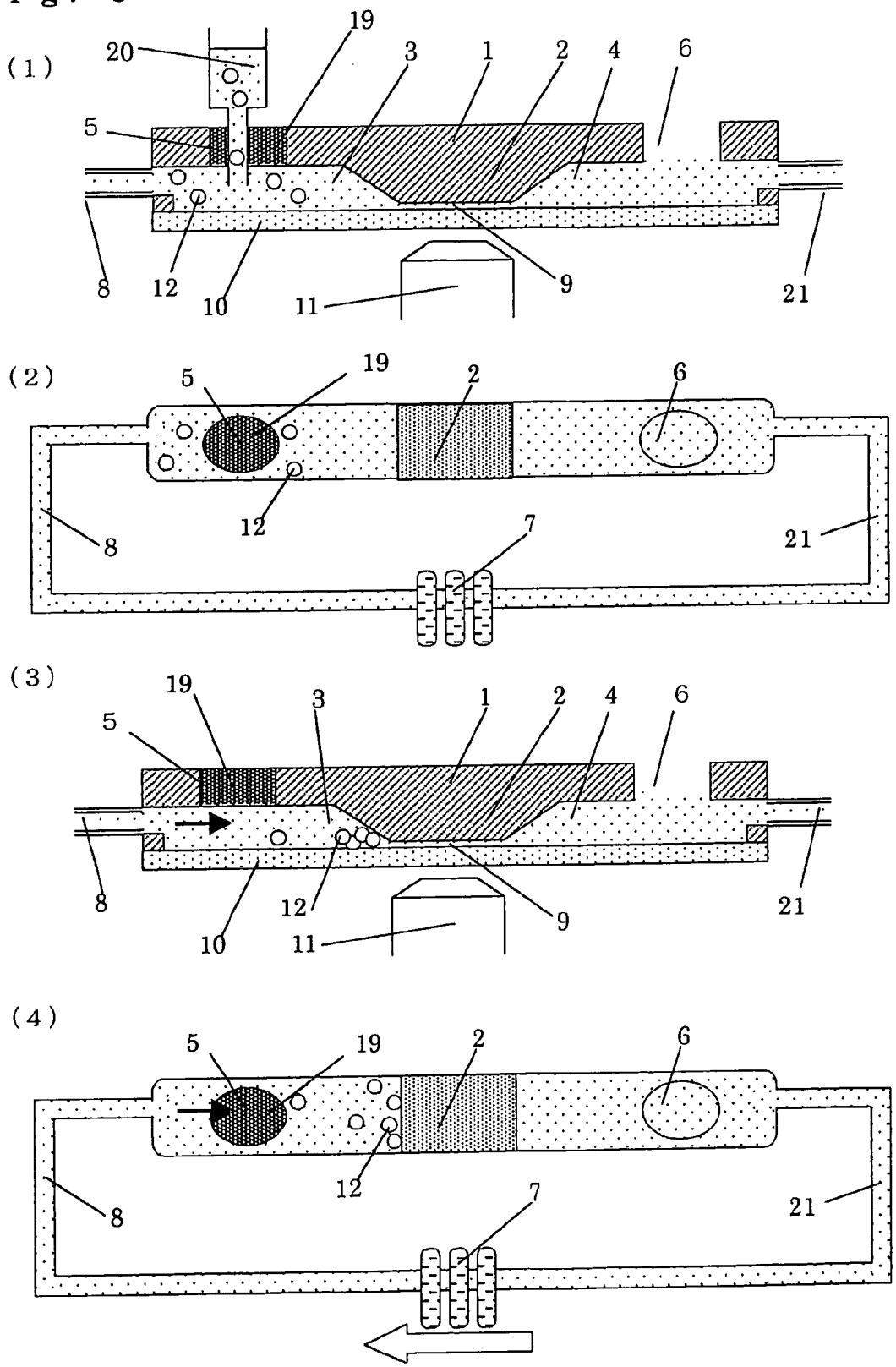
FIG. 9 is a model view showing a structure wherein a cell-injection port is sealed in the type of FIG. 8.

FIG. 9 shows an example, which is a substitute for the structure of FIG. 8, wherein a cell-injection port 5 is sealed. As FIG. 9 shows, the cell-injection port 5 can be sealed with a flexible stopper 19. Alternatively, the sealing may be made with the use of a slide-type switching member, a valve, a tap or the like.

Figure 10:
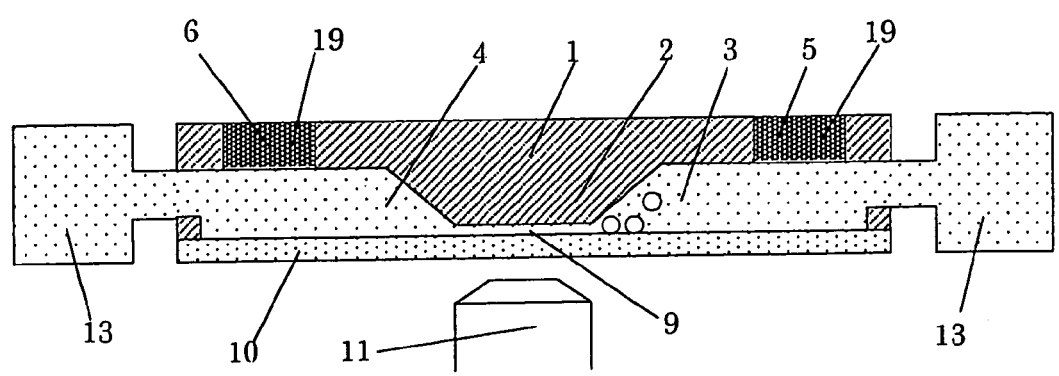
FIG. 10 is a model view showing a structure wherein a cell-injection port and a specimen-injection port are both sealed.

FIG. 10 shows another modification of the apparatus according to the present invention wherein a cell-injection port 5 and a specimen-injection port 6 are both sealed. In the case of FIG. 10, the injection ports 5 and 6 are sealed respectively with flexible stoppers 19 and cells and a factor are injected through the respective stoppers. To bring together the cells at one end of a channel 9, liquid-transport means provided with a member (for example, a syringe 13) of stopping the migration of the liquid after the liquid transportation are provided in both of the cell-holding well 3 side and the specimen-holding well 4 side. By driving these means in conjunction, a liquid is transported from the cell-holding well 3 side toward the specimen-holding well 4 side. It is needless to say that another means of sealing the injection ports such as a slide-type switching member or the like may be used as a substitute for the stopper.

In the apparatus according to the present invention as discussed above, use may be made of a structure wherein the substrate and the glass substrate are integrated together and at least one of the faces thereof has light-permeability, i.e., being transparent.

Figure 11:
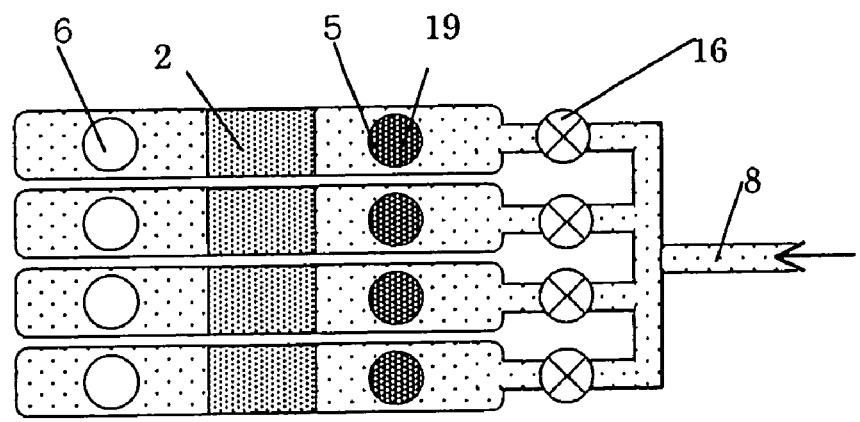
FIG. 11 is a model view showing a case wherein a plural number of units of the type shown in FIG. 6 are integrated.

Moreover, the present invention includes in its scope an integration apparatus for detecting chemotaxis of cells consisting of a plural number of units with the use of the above-described apparatus for detecting chemotaxis of cells as a single unit. For example, FIG. 11 shows a model assembly wherein units each having a sealed cell-injection port are connected via an injection pipe 8 so as to bring together the cells in individual cell-holding wells at the end of a bank at the same time. In the case of FIG. 11, it is favorable that the injection pipe 8 is sealed at individual units with, for example, valves 16 so as to ensure the sealing in the cell-injection port 5 side. The means for sealing the specimen-injection port and the pipe may be appropriately selected form among various members as cited above.

Figure 12:
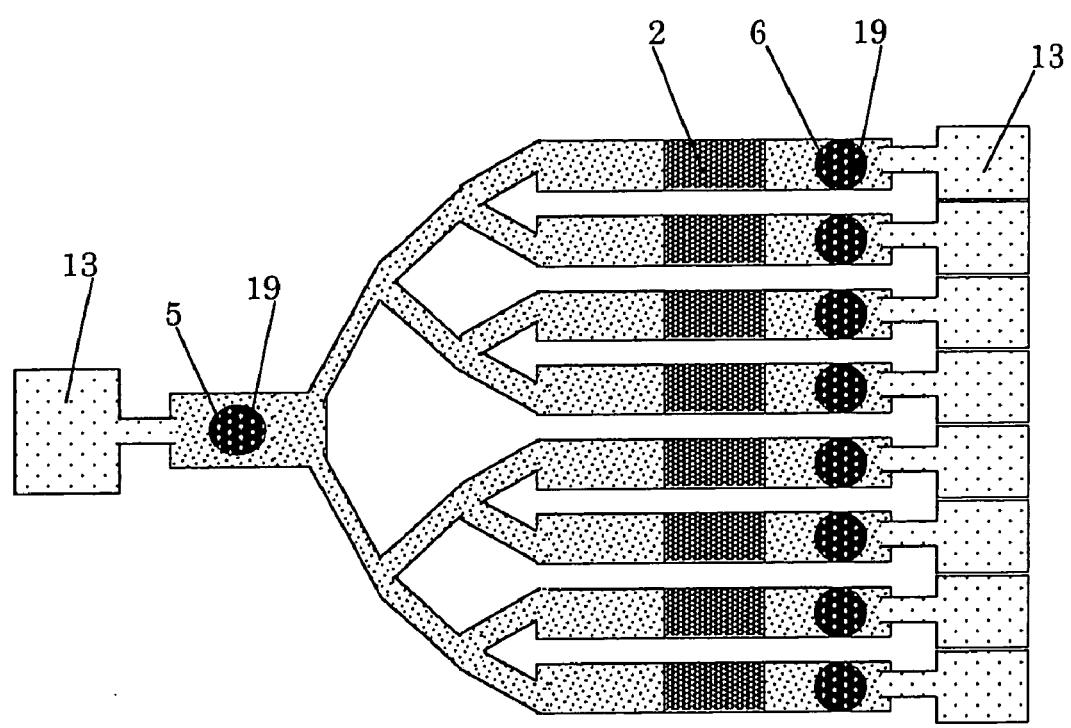
FIG. 12 is a model view showing a case wherein a plural number of units of the type shown in FIG. 10 are integrated.

FIG. 12 shows a model view of an integration apparatus having the units of the type shown in FIG. 10. Stoppers 19 in this figure may be substituted by other means. By using this apparatus, effects of various specimens on a single type of cells can be examined simultaneously. Alternatively, a cell-injection port 5 and specimen-injection ports 6 may be interchanged each other. Owing to this structure, reactions of a single specimen with various type of cells can be examined simultaneously.

Moreover, the present invention includes an integration apparatus consisting of a plural number of integration units and an integration apparatus consisting of integration units of multiplicity of types.

According to the present invention, such an apparatus can be downsized as a whole and a sample can be treated in a microquantity. By integrating a plural number of units, furthermore, a large number of specimens can be treated simultaneously. In addition, a liquid-aspiration/injection program can be easily controlled in the apparatus according to the present invention, which makes it suitable for fabricating an automated apparatus.

Next, each part of the apparatus according to the present invention will be illustrated by reference to specific examples. However, it is to be understood that these examples are intended to illustrate the present invention, not by way of limitation, and variations can be made without departing form the spirit and scope of the invention.

1) Structure of Unit

As FIG. 1 and other figures show, it is preferred that a bank 2 and wells 3 and 4 are integrally formed on a substrate 1. An optically flat glass substrate 10 is mechanically pressed against the bottom face of the substrate 1. The substrate 1 and the glass 10 may be bonded together by heating.

2) Well

The wells 3 and 4 aim at respectively holding a cell suspension and a specimen such as a chemotactic factor-containing solution or an inhibitor-containing solution. The capacity of the wells is not particularly restricted, so long as a liquid can be held therein in the minimum amount needed. For example, it is sufficient that the depth ranges from about 0.05 to about 0.1 mm, the width and the length are each about 1.2 mm.

3) Channel

Figure 13:
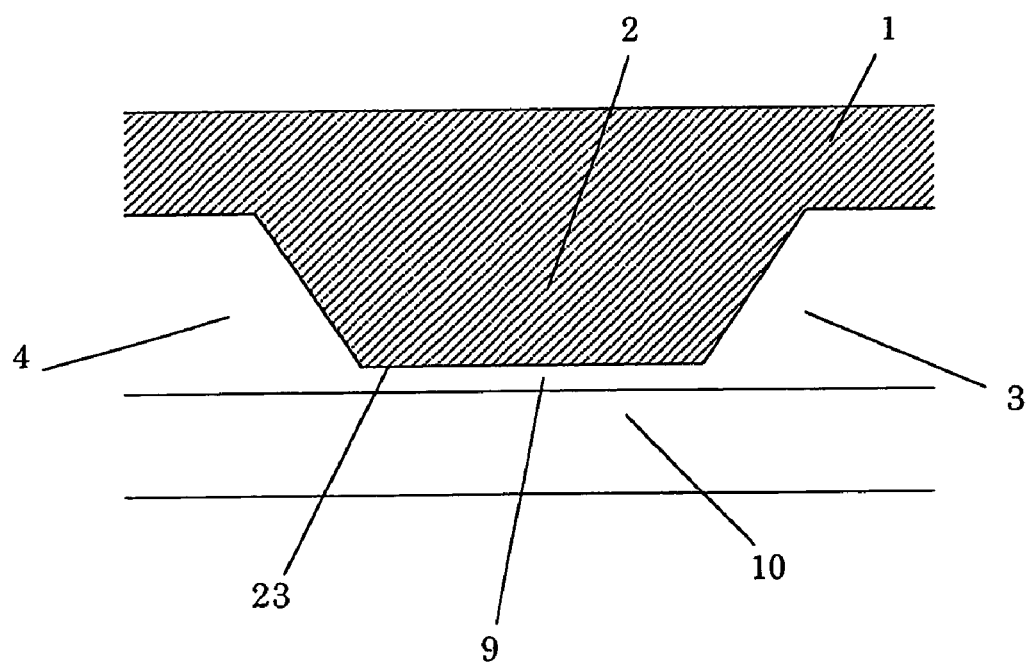
FIG. 13 is a sectional view showing an example of the structure of a bank and a channel.

Next, an example of the structure of a channel 9 (see FIG. 1) will be illustrated by referring to FIG. 13. The channel 9 is a space provided between a bank 2 (a convex on a substrate 1) partitioning the wells 3 and 4 at both ends and the glass substrate 10. A flat terrace 23 is provided on the bottom face of the bank. Although the bank 2 is not restricted in size, it is preferred, for example, that the height of the bank 2 (i.e., the distance between the glass substrate 10 and the terrace 23) ranges from about 0.003 to about 0.03 mm, while the length in the direction toward the opposite well ranges from about 0.1 to about 0.5 mm and the length in the direction orthogonal to the direction toward the opposite well is about 1.2 mm. Needless to say, these dimensional factors may be varied depending on the purpose such as the type of the subject cells.

The distance between the terrace 23 and the glass substrate 10 may be appropriately controlled depending on the cells to be treated. Usually, it ranges from 3 to 30 µm. That is to say, the distance may range from 3 to 10 µm (for example, 4, 5 or 8 µm) in the case of treating neutrophils, eosinophils, basophils, monocytes/macrophages, T cells, B cells and the like, and from 6 to 20 µm in the case of treating cancer cells and cells existing in tissues.

It is also possible to form a multistage terrace 23 to facilitate the migration of the cells toward an end of the channel 9.

Figure 14:
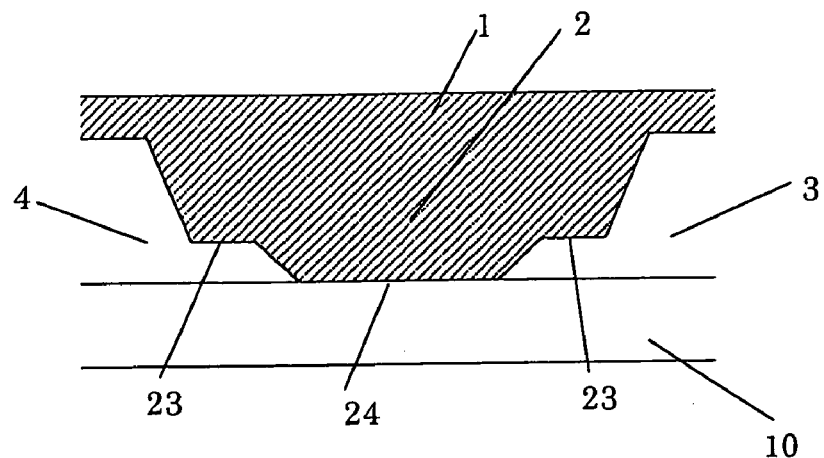
FIG. 14 shows an example of a case wherein a barrier and a groove are formed in a channel.
Figure 14:
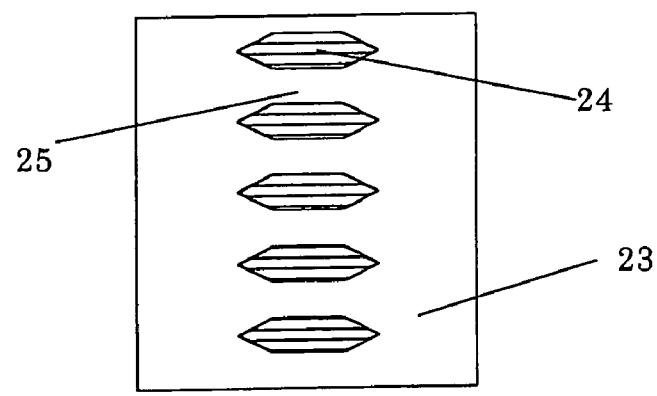
Figure 14:
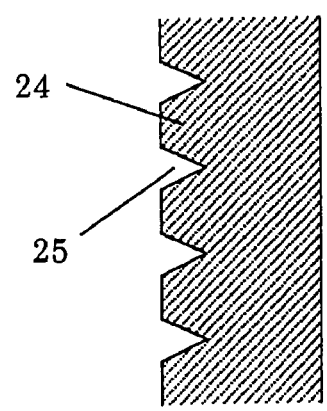

In a preferred embodiment, a plural number of barriers 24 are formed on the bottom face (the terrace 23) of the bank 2 to provide grooves 25 through which cells pass, as shown in FIGS. 14(1) and (2). FIG. 14(1) is a sectional view of the bank 2 having the barriers 24, while (2) is a top plan view showing the terrace 23, the barriers 24 and the grooves 25.

In case where barriers 24 are formed on the terrace 23, the grooves 25 provided by the barriers 24 may have an arbitrary cross-sectional shape, for example, a V-shaped section, a convex section or a semicircular section. The grooves 25 have a width and a depth fit for the diameter or deformability of cells.

FIG. 14(3) is a sectional view showing a case wherein the grooves 25 have a V-shaped section.

The width of a groove 25 usually may range from 3 to 50 µm. That is, an appropriate width may be selected depending on the cell type. The width may range from 3 to 20 µm (for example, 4, 8 or 10 µm) in the case of treating neutrophils, eosinophils, basophils, monocytes/macrophages, T cells, B cells and the like, and from 8 to 20 µm in the case of treating cancer cells and cells existing in tissues. The number of the grooves 25 is determined depending on the width of the barriers 24 and the width of the grooves 25 concerning the width of the channel 9. In case where the width of the channel 9 is 1 mm, the width of the barriers 24 is 10 µm and the width of the grooves 25 is 5 µm, for example, the number of grooves is 66 at the largest.

Figure 15:
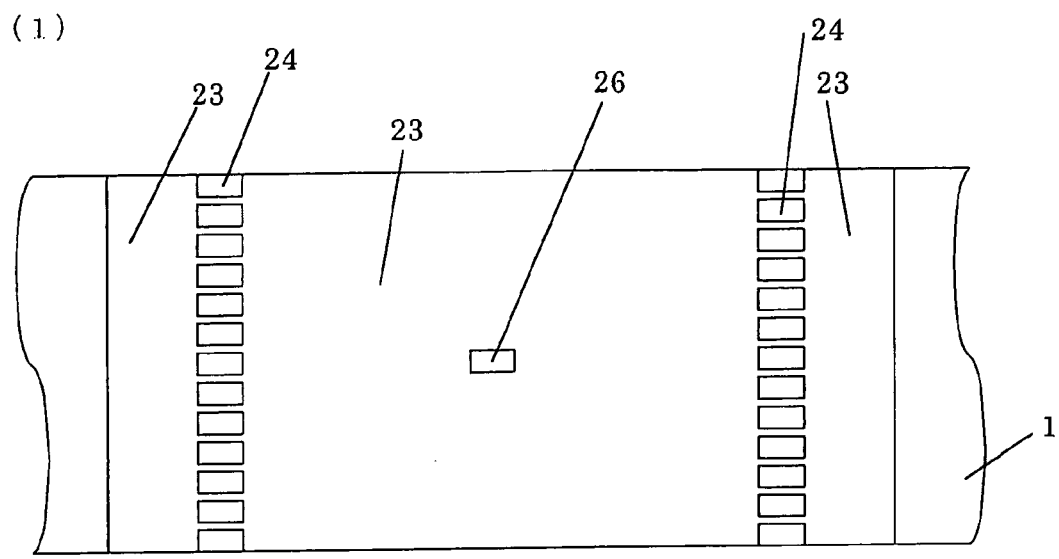
FIG. 15 shows an example wherein arrays of the barriers constituting the grooves are formed at two positions on a terrace, wherein FIG. 15(1) is a top plan view while (2) is a sectional view.
Figure 15:
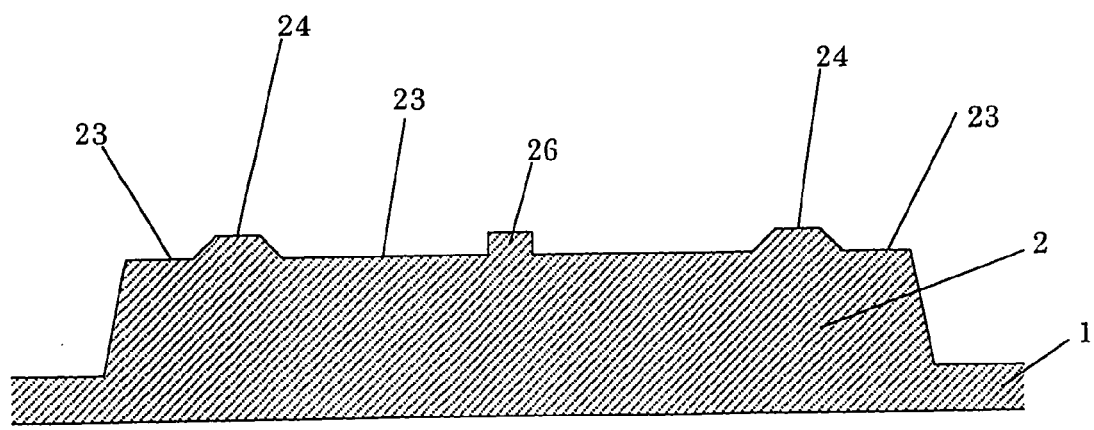

It is also possible to form arrays of barriers 24 in two positions in both sides of the terrace 23 which is formed on the bank 2 (see FIGS. 15(1) and (2)). By using this structure, cells having passed through the grooves can be easily observed and counted. By providing a mark 26 at an appropriate position in the center terrace 23, positioning can be easily made under a camera or a microscope (26 in FIG. 15). It is desirable that the terrace located at the center has an area which can be included in the microscopic field. FIG. 15(1) is a top plan view while (2) is a sectional view.

4) Construction of Well and Channel

For the substrate 1, it is preferable to use a material which can be easily fine processed and is relatively inert to cells, for example, single-crystal silicon. The barriers 24 and the grooves 25 can be easily constructed by subjecting the single-crystal silicon to photolithography or etching (for example, wet etching or dry etching) employed in manufacturing integrated circuits. The wells 3 and 4, which are relatively larger than the barriers 24 and the grooves 25, can be constructed by using various known engineering techniques such as sand blasting and dry etching.

In addition to single-crystal silicon, use can be made of hard glasses, hard plastics, metals, etc., so long as a microstructure can be constructed in the channel. Polydimethylsiloxane (PDMS) may be cited as an example of the plastics suitable for the construction of a microstructure. In the case of using plastics, it is preferable to employ a treatment for making the surface hydrophilic, for example, forming a hydrophilic film on the surface. To facilitate the observation of the cells, it is also preferable to subject the surface at least having the terrace 23 to specular finishing by, for example, silver deposition. It is also possible to separately construct the bank 2 and the wells 3 and 4 and then combine them together.

5) Glass Substrate

As shown in FIG. 1 and other figures, the glass substrate 10 is tightly pressed against the substrate 1 to provide a space in which a liquid is held, thereby enabling the observation of cells passing through the channels. Thus, the glass substrate 10 should remain optically transparent and flat and provide a plane to which cells can adhere. Use can be made therefor of glass as well as plastics such as transparent acrylic resins, so long as the above objects can be achieved thereby. Although its thickness is not particularly restricted so long as no strain arises in the step of pressing against the substrate, the thickness adequately ranges from 0.1 to 2 mm. In the case where cellular constituents are fluorescent labeled and observed, a thinner glass substrate 10 is preferred.

In the case where the substrate 1 is made of a silicone wafer, it can be integrated together with the glass substrate 10 by mechanically pressing. Alternatively, they may be bonded together by heating to 200 to 400° C. In this case, however, it is needed to select materials for the substrate 1 and the glass substrate 10 so that the coefficients of thermal expansion and the coefficients of thermal shrinkage thereof agree with each other.

6) Pipe

It is generally preferred that the injection pipe 8 and the aspiration discharge pipe 21 are made of flexible materials. In the case of using a pulse pump 7, it is particularly needed that these pipes follow-up minor movements. Use can be made of, for example, PDMS, polyethylene, vinyl chloride, etc. therefor.

7) Arrangement of a Plural Number of Units

By referring two wells connected to each other via a channel as a single unit, a plural number of units may be arranged and integrated on a single substrate. Thus, an apparatus whereby a large number of specimens can be simultaneously treated can be obtained. Units of the same type may be arranged in parallel or units of different types may be arranged. Namely, arbitrary arrangement may be employed depending on the purpose. In the case where a unit having two wells connected to each other via a channel has a major side length of 2.9 mm and a minor side length of 1.2 mm, for example, 14 (i.e., 7 in column×4 in row) can be provided at intervals of 0.8 mm on a rectangular substrate of 16 mm in width and 10 mm in length.

Such assemblies consisting of a plural number of units as described above may be further integrated. It is also possible to integrate different types of units together.

In the case of integrating a plural number of units, use may be made of one glass substrate 10 covering all of the units.

8) Detection Means

The detection means to be used in the present invention may be any means so long as cells which are passing through the channel 9 or have migrated therethrough can be detected thereby. If necessary, it involves a means of recording the detection data. Any means known as a means of detecting and recording cells is usable therefor. Use can be made of, for example, a microscope optionally combined with a video camera. It is also possible to employ a system having an objective lens provided with a CCD camera. For the detection in integrated units, it is preferable to employ a system wherein the channels of the units are successively scanned along with an objective lens.

As shown in FIG. 1 etc., the detection means is usually provided below the channel 9 in a unit. In an automated apparatus having a plural number of units integrated together, it is also possible to employ a system wherein arrays of the units successively come to a detection part located at a definite position for detection and recording. In this case, the channels of the aligned units are scanned with the detector. Either one or more scanning detectors 11 may be employed. Owing to this constitution, a relatively small number of detectors suffice for the detection in a plural number of integrated units.

Cells which are passing or have passed through the channel 9 can be detected and counted by directly observing the cells with a microscope. Alternatively, the detection and counting can be easily performed by preliminarily labeling the cells with a luminous or fluorescent substance and then capturing the luminescence or fluorescence in a conventional manner.

9) Automatic Controlling System

The apparatus according to the present invention can be easily controlled automatically. For example, use can be made of an autopipette whereby injection, transportation and discharge of cells or specimens such as a factor can be controlled with a computer, a pulse pump or a syringe driven by a stepping motor as a means of transporting a liquid, and a slide-type switching member for opening and closing an injection port. Thus, the operation order and the operation level of each member can be controlled by computerized programming. In the case of using a stopper as a substitute for the slide-type switching member for opening and closing an injection port, it is unnecessary to control the switching operation.

In an integrated apparatus, it is preferable to employ a pipette having a multichannel syringe.

INDUSTRIAL APPLICABILITY

According to the structure of the present invention, it is possible to control the positioning of cells injected into a channel and bring together and align the cells at an end of the channel. It is also possible thereby to hold the cells in the above-described state and maintain a stable concentration gradient due to the diffusion of the specimen such as a chemotactic factor in a channel. Accordingly, quantitative data certainly reflecting the effect of a chemotactic factor or an inhibitor and the properties of cells can be obtained.

By employing the structure according to the present invention, it is also possible to prevent disorders in the cell line and in the concentration gradient of a specimen formed in the channel even though the apparatus is unexpectedly vibrated. Thus, the movements of the cells can be exactly understood.

By using the structure according to the present invention, furthermore, the apparatus can be downsized. When this apparatus is applied to an apparatus for detecting chemotaxis of cells or separating chemotactic cells, namely, samples can be used in an amount ⅟500 to ⅟1000 times as much in the conventional cases with the use of a Boyden chamber. That is to say, a biological sample such as whole blood per se can be used as a sample in the apparatus according to the present invention. In the case of using whole blood as a sample, for example, measurement can be made by using 0.1 µl or less of the blood in the case of detecting the chemotaxis of neutrophils and about 1 µl of the blood in the case of detecting eosinophils, monocytes or basophils.

The structure according to the present invention achieves a remarkable technical merit that the positioning of cells in a well can be delicately controlled and thus the apparatus can be easily automated.

The unit of the apparatus according to the present invention can be in a microsize and thus a plural number of the units can be integrated together, which brings about another merit that an apparatus whereby a large number of samples can be simultaneously treated can be fabricated. In this case, an apparatus having an automated system of injecting and detecting liquids can be easily fabricated.

In integrating a plural number of units, detection and separation for different purposes can be simultaneously carried out by combining and integrating units of different types together. Thus, the treatment efficiency can be elevated. In the case of an apparatus for detecting chemotaxis of cells, for example, the detection of various chemotactic factors or inhibitors for a single type of cells or the detection of the chemotaxis of different types of cells for a single chemotactic factor can be carried out at once.

The invention claimed is:

1. A apparatus for detecting chemotaxis of cells which comprises:
   a cell-holding well having an opening for injecting cells;
   a specimen-holding well having an opening for injecting a specimen;
   a channel which connects said cell-holding well and specimen-holding well up with each other and has resistance to the passage of cells, and which detects chemotaxis of cells by observing a passage of cells in said channel from said cell-holding well to said specimen-holding well caused by a concentration gradient of said specimen formed in a stationary liquid in said channel;
   a means of transporting said liquid from said cell-holding well to said specimen-holding well by an injection or an aspiration discharge of said liquid and then stopping the transportation of said liquid after said injection or said aspiration discharge of said liquid in order to control a position of each cell in said cell-holding well; and
   a means of sealing said opening(s) in one or both of said cell-holding well and said specimen-holding well for preventing said liquid from an unexpected transportation thereof in said channel while detecting chemotaxis of cells,
   wherein said cell-holding well and said specimen-holding well are connected via an injection pipe joined to said cell-holding well, an aspiration discharge pipe joined to said specimen-holding well and said means of transporting a liquid, and a stopper to stop the transportation thereof between said pipes, to form a structure in which said liquid is circulated.

2. The apparatus for detecting chemotaxis of cells as claimed in claim 1, wherein a specimen-injection port is sealed with a flexible stopper, and wherein said injection pipe and said aspiration discharge pipe are connected by a means of transporting which circulates a liquid in a single direction.

3. An apparatus for detecting chemotaxis of cells which comprises:
   a cell-holding well having an opening for injecting cells;
   a specimen-holding well having an opening for injecting a specimen;
   a channel which connects said cell-holding well and specimen-holding well up with each other and has resistance to the passage of cells, and which detects chemotaxis of cells by observing a passage of cells in said channel from said cell-holding well to said specimen-holding well caused by a concentration gradient of said specimen formed in a stationary liquid in said channel;
   a means of transporting said liquid from said cell-holding well to said specimen-holding well by an injection or an aspiration discharge of said liquid and then stopping the transportation of said liquid after said injection or said aspiration discharge of said liquid in order to control a position of each cell in said cell-holding well; and a means of sealing said opening(s) in one or both of said cell-holding well and said specimen-holding well for preventing said liquid from an unexpected transportation thereof in said channel while detecting chemotaxis of cells;

wherein said cell-holding well and said specimen-holding well are connected via an injection pipe joined to said cell-holding well, an aspiration discharge pipe joined to said specimen-holding well and said means of transporting a liquid, and a stopper to stop the transportation thereof between said pipes, to form a structure in which said liquid is circulated.

4. The apparatus for detecting chemotaxis of cells as claimed in claim 3, wherein said means of transporting a liquid and stopping the transportation thereof is a pulse pump or a syringe.

5. The apparatus for detecting chemotaxis of cells as claimed in claim 3, wherein said means of sealing the opening is a member selected from the group consisting of a flexible stopper, a slide-type switching member, a tap, a valve and a combination thereof.

6. The apparatus for detecting chemotaxis of cells as claimed in claim 3, wherein said means of sealing is a means of sealing said openings in both of said cell-holding well and said specimen-holding well, and said opening in said specimen-holding well is closed when said opening in said cell-holding well is opened and then said opening in said cell-holding well is closed when said opening in said specimen-holding well is opened.

7. The apparatus for detecting chemotaxis of cells as claimed in claim 3, wherein plural number of units, each of which units comprises said cell-holding well, said specimen-holding well and said channel, are connected to only one means of transporting a liquid and a stopper to stop the transportation thereof via said injection pipe so as to control a position of each cell in said individual cell-holding well.

8. The apparatus for detecting chemotaxis of cells as claimed in claim 6, wherein said means of sealing is a slide-type switching member.

9. An integration apparatus for detecting chemotaxis of cells which consists of a plural number of units with use of said apparatus for detecting chemotaxis of cells as claimed in claim 3 as a single unit.

10. An apparatus for detecting chemotaxis of cells which comprises:

a cell-holding well having an opening for injecting cells;

a specimen-holding well having an opening for injecting a specimen;

a channel which connects said cell-holding well and specimen-holding well up with each other and has resistance to the passage of cells, and which detects chemotaxis of cells by observing a passage of cells in said channel from said cell-holding well to said specimen-holding well caused by a concentration gradient of said specimen formed in a stationary liquid in said channel;

a means of transporting said liquid from said cell-holding well to said specimen-holding well by an injection or an aspiration discharge of said liquid and then stopping the transportation of said liquid after said injection or said aspiration discharge of said liquid in order to control a position of each cell in said cell-holding well; and a means of sealing said opening(s) in one or both of said cell-holding well and said specimen-holding well for preventing said liquid from an unexpected transportation thereof in said channel while detecting chemotaxis of cells;

wherein said cell-holding well has an injection pipe while a specimen-holding well has an aspiration discharge pipe and a specimen-injection port is sealed with a flexible stopper, and wherein said injection pipe and said aspiration discharge pipe are connected by a means of transporting which circulates a liquid in a single direction.

11. The apparatus for detecting chemotaxis of cells as claimed in claim 10, wherein said means of transporting a liquid and stopping the transportation thereof is a pulse pump or a syringe.

12. The apparatus for detecting chemotaxis of cells as claimed in claim 10, wherein said means of sealing the opening is a member selected from the group consisting of a flexible stopper, a slide-type switching member, a tap, a valve and a combination thereof.

13. The apparatus for detecting chemotaxis of cells as claimed in claim 10, wherein said means of sealing is a means of sealing said openings in both of said cell-holding well and said specimen-holding well, and said opening in said specimen-holding well is closed when said opening in said cell-holding well is opened and then said opening in said cell-holding well is closed when said opening in said specimen-holding well is opened.

14. The apparatus for detecting chemotaxis of cells as claimed in claim 10, wherein plural number of units, each of which units comprises said cell-holding well, said specimen-holding well and said channel, are connected to only one means of transporting a liquid and a stopper to stop the transportation thereof via said injection pipe so as to control a position of each cell in said individual cell-holding well.

15. The apparatus for detecting chemotaxis of cells as claimed in claim 13, wherein said means of sealing is a slide-type switching member.

16. An integration apparatus for detecting chemotaxis of cells which consists of a plural number of units with use of said apparatus for detecting chemotaxis of cells as claimed in claim 10 as a single unit.

17. An apparatus for detecting chemotaxis of cells which comprises:

a cell-holding well having an opening for injecting cells;

a specimen-holding well having an opening for injecting a specimen;

a channel which connects said cell-holding well and specimen-holding well up with each other and has resistance to the passage of cells, and which detects chemotaxis of cells by observing a passage of cells in said channel from said cell-holding well to said specimen-holding well caused by a concentration gradient of said specimen formed in a stationary liquid in said channel;

a means of transporting said liquid from said cell-holding well to said specimen-holding well by an injection or an aspiration discharge of said liquid and then stopping the transportation of said liquid after said injection or said aspiration discharge of said liquid in order to control a position of each cell in said cell-holding well; and a means of sealing said opening(s) in one or both of said cell-holding well and said specimen-holding well for preventing said liquid from an unexpected transportation thereof in said channel while detecting chemotaxis of cells;

wherein said cell-holding well having an opening for injecting cells and a specimen-holding well having an opening for injecting a specimen which are formed by a substrate having a raised bank in the middle thereof and a glass substrate and are divided into each other by said raised bank.

18. The apparatus for detecting chemotaxis of cells as claimed in claim 17, wherein said means of transporting a liquid and stopping the transportation thereof is a pulse pump or a syringe.

19. The apparatus for detecting chemotaxis of cells as claimed in claim 17, wherein said means of sealing the opening is a member selected from the group consisting of a flexible stopper, a slide-type switching member, a tap, a valve and a combination thereof.

20. The apparatus for detecting chemotaxis of cells as claimed in claim 17, wherein
said means of sealing is a means of sealing said openings in both of said cell-holding well and said specimen-holding well, and said opening in said specimen-holding well is closed when said opening in said cell-holding well is opened and then said opening in said cell-holding well is closed when said opening in said specimen-holding well is opened.

21. The apparatus for detecting chemotaxis of cells as claimed in claim 17, wherein said cell-holding well and said specimen-holding well are connected via an injection pipe joined to said cell-holding well, an aspiration discharge pipe joined to said specimen-holding well and said means of transporting a liquid, and a stopper to stop the transportation thereof between said pipes, to form a structure in which said liquid is circulated.

22. The apparatus for detecting chemotaxis of cells as claimed in claim 17, wherein plural number of units, each of which units comprises said cell-holding well, said specimen-holding well and said channel, are connected to only one means of transporting a liquid and a stopper to stop the transportation thereof via said injection pipe so as to control a position of each cell in said individual cell-holding well.

23. The apparatus for detecting chemotaxis of cells as claimed in claim 20, wherein said means of sealing is a slide-type switching member.

24. The apparatus for detecting chemotaxis of cells as claimed in claim 17, wherein said cell-holding well has an injection pipe while a specimen-holding well has an aspiration discharge pipe and a specimen-injection port is sealed with a flexible stopper, and wherein said injection pipe and said aspiration discharge pipe are connected by a means of transporting which circulates a liquid in a single direction.

* * * * *